(12) United States Patent
Liu (10) Patent No.: US 9,373,392 B2
(45) Date of Patent: *Jun. 21, 2016

(54) MEMORY CELLS WITH RECTIFYING DEVICE

(71) Applicant: Micron Technology, Inc., Boise, ID (US)

(72) Inventor: Jun Liu, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/599,905

(22) Filed: Jan. 19, 2015

(65) Prior Publication Data

US 2015/0131362 A1   May 14, 2015

Related U.S. Application Data

(60) Continuation of application No. 13/158,836, filed on Jun. 13, 2011, now Pat. No. 8,947,923, which is a division of application No. 12/026,195, filed on Feb. 5, 2008, now Pat. No. 7,961,506.

(51) Int. Cl.
 *G11C 13/00* (2006.01)
 *H01L 27/102* (2006.01)
 (Continued)

(52) U.S. Cl.
 CPC .......... *G11C 13/0004* (2013.01); *G11C 13/003* (2013.01); *G11C 13/0023* (2013.01); *H01L 27/1021* (2013.01); *G11C 5/025* (2013.01); *G11C 5/063* (2013.01);
 (Continued)

(58) Field of Classification Search
 CPC .... G11C 5/025; G11C 5/063; G11C 13/0004; G11C 13/0023; G11C 13/003; G11C 2213/72; G11C 2213/74; G11C 2213/78; G11C 2213/79; H01L 27/1021
 See application file for complete search history.

(56) References Cited

U.S. PATENT DOCUMENTS

| 4,809,044 A | 2/1989 | Pryor et al. |
| 5,515,317 A | 5/1996 | Wells et al. |

(Continued)

FOREIGN PATENT DOCUMENTS

| JP | 2007067013 | 3/2007 |
| TW | 200802362 A | 1/2008 |

(Continued)

OTHER PUBLICATIONS

"Chinese Application Serial No. 200980104178.8, Office Action mailed May 4, 2012", 9 pgs, Provided in U.S. Appl. No. 13/158,836.
(Continued)

*Primary Examiner* — Harry W Byrne
*Assistant Examiner* — Lance Reidlinger
(74) *Attorney, Agent, or Firm* — Schwegman Lundberg & Woessner, P.A.

(57) ABSTRACT

Memory devices and methods described are shown that provide improvements, including improved cell isolation for operations such as read and write. Further, methods and devices for addressing and accessing cells are shown that provide a simple and efficient way to manage devices with multiple cells associated with each access transistor. Examples of multiple cell devices include phase change memory devices with multiple cells associated with each access transistor.

18 Claims, 11 Drawing Sheets

(51) Int. Cl.
    *G11C 5/02*  (2006.01)
    *G11C 5/06*  (2006.01)
(52) U.S. Cl.
    CPC ....... *G11C 2213/72* (2013.01); *G11C 2213/74* (2013.01); *G11C 2213/78* (2013.01); *G11C 2213/79* (2013.01)

(56) References Cited

U.S. PATENT DOCUMENTS

| | | |
|---|---|---|
| 5,574,879 A | 11/1996 | Wells et al. |
| 5,764,588 A | 6/1998 | Nogami et al. |
| 5,896,340 A | 4/1999 | Wong et al. |
| 5,966,340 A | 10/1999 | Fujino et al. |
| 5,973,356 A | 10/1999 | Noble et al. |
| 6,021,064 A | 2/2000 | McKenny et al. |
| 6,072,713 A | 6/2000 | McKenny et al. |
| 6,143,636 A | 11/2000 | Forbes et al. |
| 6,285,593 B1 | 9/2001 | Wong |
| 6,418,049 B1 | 7/2002 | Kozicki et al. |
| 6,456,524 B1 | 9/2002 | Perner et al. |
| 6,587,372 B2 | 7/2003 | Blodgett |
| 6,654,280 B2 | 11/2003 | Blodgett |
| 6,662,263 B1 | 12/2003 | Wong |
| 6,731,535 B1 | 5/2004 | Ooishi et al. |
| 6,765,261 B2 | 7/2004 | Widdershoven |
| 6,778,445 B2 | 8/2004 | Ooishi et al. |
| 6,816,408 B2 | 11/2004 | Blodgett |
| 6,894,941 B2 | 5/2005 | Kurjanowicz et al. |
| 6,901,007 B2 | 5/2005 | Blodgett |
| 6,937,505 B2 | 8/2005 | Morikawa |
| 7,026,639 B2 | 4/2006 | Cho et al. |
| 7,154,798 B2 | 12/2006 | Lin et al. |
| 7,205,564 B2 | 4/2007 | Kajiyama |
| 7,215,568 B2 | 5/2007 | Liaw et al. |
| 7,236,393 B2 | 6/2007 | Cho et al. |
| 7,307,268 B2 | 12/2007 | Scheuerlein |
| 7,400,521 B1 | 7/2008 | Hoenigschmid |
| 7,436,693 B2 | 10/2008 | Kang et al. |
| 7,440,308 B2 | 10/2008 | Jeong et al. |
| 7,545,019 B2 | 6/2009 | Philipp et al. |
| 7,560,723 B2 | 7/2009 | Liu |
| 7,675,770 B2 | 3/2010 | Asano et al. |
| 7,791,058 B2 | 9/2010 | Liu |
| 7,817,454 B2 | 10/2010 | Liu |
| 7,961,506 B2 | 6/2011 | Liu |
| 8,947,923 B2 | 2/2015 | Liu |
| 2001/0050866 A1 | 12/2001 | Khieu |
| 2003/0043621 A1 | 3/2003 | Wong |
| 2004/0114428 A1 | 6/2004 | Morikawa |
| 2004/0179397 A1 | 9/2004 | Banks |
| 2005/0135146 A1 | 6/2005 | Taussig et al. |
| 2005/0146955 A1 | 7/2005 | Kajiyama |
| 2005/0243598 A1 | 11/2005 | Lin et al. |
| 2006/0050547 A1 | 3/2006 | Liaw |
| 2006/0154432 A1 | 7/2006 | Arai et al. |
| 2006/0176724 A1 | 8/2006 | Asano et al. |
| 2006/0220071 A1 | 10/2006 | Kang et al. |
| 2006/0221687 A1 | 10/2006 | Banks |
| 2007/0020849 A1 | 1/2007 | Hong et al. |
| 2007/0054452 A1 | 3/2007 | Hong et al. |
| 2007/0103963 A1 | 5/2007 | Kim et al. |
| 2007/0133270 A1 | 6/2007 | Jeong et al. |
| 2007/0159867 A1 | 7/2007 | Muraoka et al. |
| 2007/0217254 A1 | 9/2007 | Matsuoka et al. |
| 2007/0246766 A1 | 10/2007 | Liu |
| 2008/0198644 A1 | 8/2008 | Broms et al. |
| 2008/0296554 A1 | 12/2008 | Lee |
| 2008/0298113 A1 | 12/2008 | Liu et al. |
| 2009/0196095 A1 | 8/2009 | Liu |
| 2009/0267044 A1 | 10/2009 | Chang |
| 2010/0270529 A1 | 10/2010 | Lung |
| 2010/0295011 A1 | 11/2010 | Liu |
| 2011/0255331 A1 | 10/2011 | Liu |

FOREIGN PATENT DOCUMENTS

| | | |
|---|---|---|
| WO | WO-2004027877 A1 | 1/2004 |
| WO | WO-2008150583 A2 | 12/2008 |
| WO | WO-2009099626 A1 | 8/2009 |

OTHER PUBLICATIONS

"Chinese Application Serial No. 200980104178.8, Response filed Nov. 19, 2012 to Office Action mailed May 4, 2012", 9 pgs, Provided in U.S. Appl. No. 13/158,836.

"European Application Serial No. 09708959.3, Examination Notification Art. 94(3) mailed Jul. 30, 2013", 5 pgs, Provided in U.S. Appl. No. 13/158,836.

"European Application Serial No. 09708959.3, Extended Search Report mailed Jun. 14, 2012" 10 pgs, Provided in U.S. Appl. No. 13/158,836.

"European Application Serial No. 09708959.3, Response filed Jan. 14, 2013 to European Search Report mailed Jun. 14, 2012", 8 pgs, Provided in U.S. Appl. No. 13/158,836.

"International Application Serial No. PCT/US2009/000738, Search Report and Written Opinion mailed Jun. 29, 2009", 11 pgs, Provided in U.S. Appl. No. 12/026,195.

"Micron Technical Note: Hamming Codes for NAND Flash Memory Devices", Micron Technical Note, TN-29-08, http://download.micron.com/pdf/technotes/nand/tn2908.pdf., (2005), 7 pages, Provided in U.S. Appl. No. 12/026,195.

"Taiwanese Application Serial No. 098103716, Office Action mailed Mar. 27, 2013", 12 pgs, Provided in U.S. Appl. No. 13/158,836.

"Technical Note: High-Speed Programming Performance and Write Buffer Comman Sequence", Micron Technical Note, TN-28-42, Write Buffer Command Sequence, http://download.micron.com/pdf/technotes/FT42.pdf, (2002), 3 pages, Provided in U.S. Appl. No. 12/026,195.

Mandelman, J. A., et al., "Challenges and Future Directions for the Scaling of Dynamic Random-Access Memory (DRAM)", IBM Journal of R&D, vol. 46, No. 2/3, http://www.research.ibm.com/journal/rd/462/mandelman.html, (Mar./May 2002), 187-212, Provided in U.S. Appl. No. 12/026,195.

"Korean Application Serial No. 10-2010-7019843 Response filed Feb. 27, 2015 to Office Action mailed Dec. 31, 2014", With the English claims, 23 pgs.

"Taiwanese Application Serial No. 102128386, Office Action mailed Oct. 6, 2015", 5 pgs.

MEMORY CELLS WITH RECTIFYING DEVICE

PRIORITY APPLICATION

This application is a continuation of U.S. application Ser. No. 13/158,836, filed Jun. 13, 2011, which is a divisional of U.S. application Ser. No. 12/026,195, filed Feb. 5, 2008, now issued as U.S. Pat. No. 7,961,506, all of which are incorporated herein by reference in their entirety.

TECHNICAL FIELD

This application relates generally to memory devices for storing data. A specific example of a memory device described in the present disclosure includes a memory with multiple memory cells associated with a given access transistor, wherein the memory cells are part of a structure such as a phase change memory device.

BACKGROUND

There is an increasing demand for more memory capability on smaller chips in the semiconductor memory industry. Manufacturers are constantly trying to reduce the size of electronic components such as transistors, flash cells, memory bit storage devices etc. on memory chips to improve density and increase capacity. Also an increase in data access speed and an increase in data write speed are desirable.

DETAILED DESCRIPTION

In the following detailed description of the invention, reference is made to the accompanying drawings that form a part hereof and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

The terms "wafer" and "substrate" used in the following description include any structure having an exposed surface with which to form an integrated circuit (IC) structure of the invention. The term substrate is understood to include semiconductor wafers. The term substrate is also used to refer to semiconductor structures during processing and may include other layers, such as silicon-on-insulator (SOI), etc. that have been fabricated thereupon. Both wafer and substrate include doped and undoped semiconductors, epitaxial semiconductor layers supported by a base semiconductor or insulator, as well as other semiconductor structures well known to one skilled in the art. The term conductor is understood to include semiconductors and the term insulator or dielectric is defined to include any material that is less electrically conductive than the materials referred to as conductors.

The term "horizontal" as used in this application is defined as a plane parallel to the conventional plane or surface of a wafer or substrate, regardless of the orientation of the wafer or substrate. The term "vertical" refers to a direction perpendicular to the horizontal as defined above. Prepositions, such as "on," "side" (as in "sidewall"), "higher," "lower," "over," and "under" are defined with respect to the conventional plane or surface being on the top surface of the wafer or substrate, regardless of the orientation of the wafer or substrate.

Figure 1A:
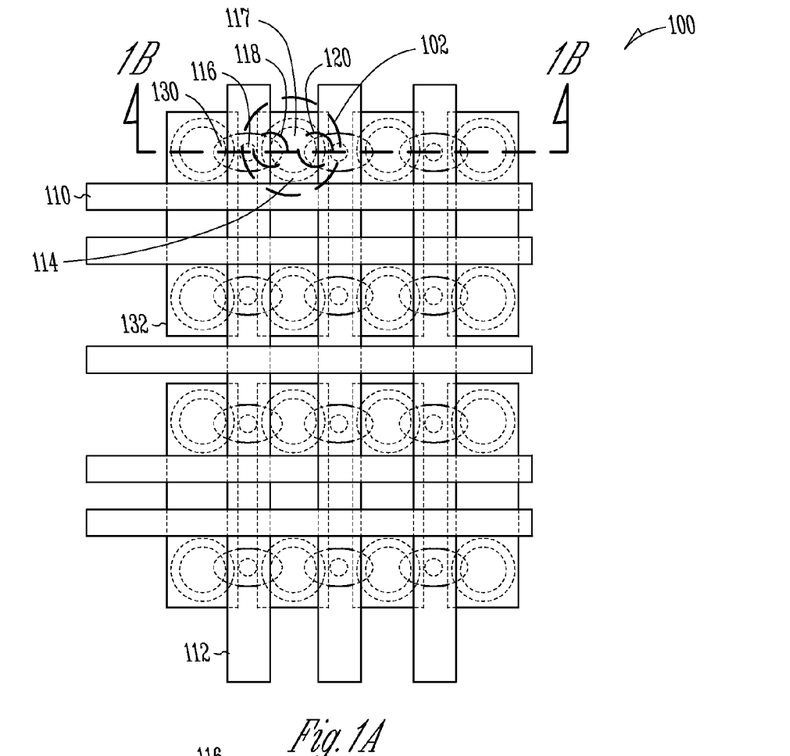
FIG. 1A shows a top view of a memory device according to an embodiment of the invention.

FIG. 1A shows a portion of a memory array 100. The illustration in figures such as 1A are not necessarily drawn to scale, and are presented in to illustrate a rough idea of the physical architecture of the memory array 100. A block 102 is shown in the array 100. The block 102 is a multi-cell block that includes a first cell 118 and a second cell 120 associated with a single access transistor as will be shown in more detail in subsequent figures. A number of access lines such as access lines 110 are shown in the array 100 that are used to activate gates of access transistors associated with each block 102.

In one embodiment, the block 102 includes a phase change memory block. A phase change structure 114 is shown comprising the first cell 118 and the second cell 120. An example of a phase change material that could be used to form the phase change structure 114 includes a chalcogenide glass, although the invention is not so limited. A number of electrode select lines 112 are shown coupled to the cells in the array 100 such as the first cell 118 and the second cell 120.

Figure 1B:
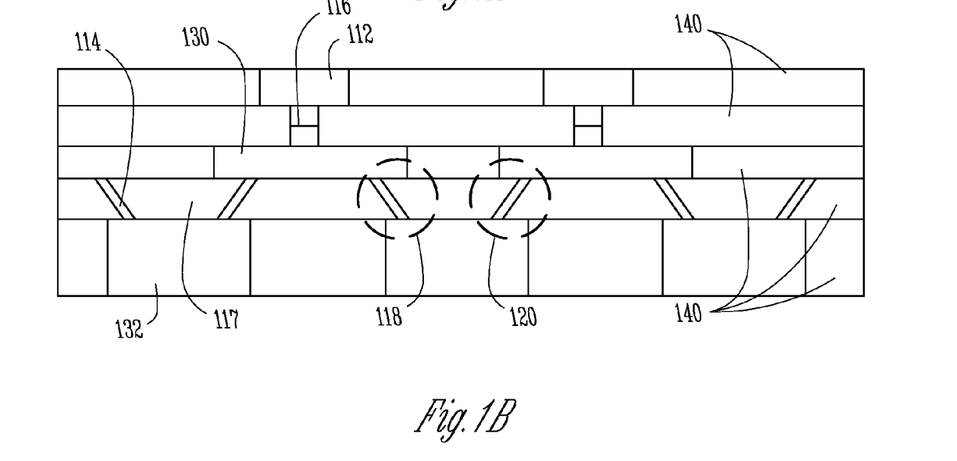
FIG. 1B shows a cross section of the memory device from FIG. 1A sectioned along line 1B-1B.

FIG. 1B illustrates the connection between the electrode select lines 112 and the components of the individual cells. The example cells 118 and 120 are shown in FIG. 1B. A first electrode 130 is shown coupled to the phase change structure 114, which is in turn coupled to a second electrode 132.

In operation, a phase of all or a portion of the phase change structure 114 is selected to correspond to a memory state, such as to provide a zero or a one designation in the logic of the memory array 100. In one embodiment, the phase of all, or a portion of a cell of the phase change structure 114 is altered between an amorphous state and a crystalline state. The respective phase states possess different electronic properties such as resistivity, therefore changing from one state to the other has the effect of programming the cell.

A dielectric 117 is shown adjacent to the phase change structure 114 to provide electrical isolation. In the example shown, the phase change structure 114 includes a ring like structure, or a structure having a perimeter, although other structures could be used, such as a cross like structure as illustrated in embodiments described below. In one example, geometry for the phase change structure 114 is selected to facilitate placement of other circuitry, such as electrode select lines, in an efficient manner to provide higher device density.

A rectifying device 116 is also shown in FIGS. 1A and 1B. Examples of rectifying devices include, but are not limited to, diodes, gate coupled field effect transistors, etc. One of ordinary skill in the art, having the benefit of the present disclosure, will recognize that any of a number of rectifying devices are possible. The rectifying device 116 is located between the electrode select line 112 and the first electrode 130. This configuration provides operational characteristics that will be discussed in more detail below.

Figure 1C:
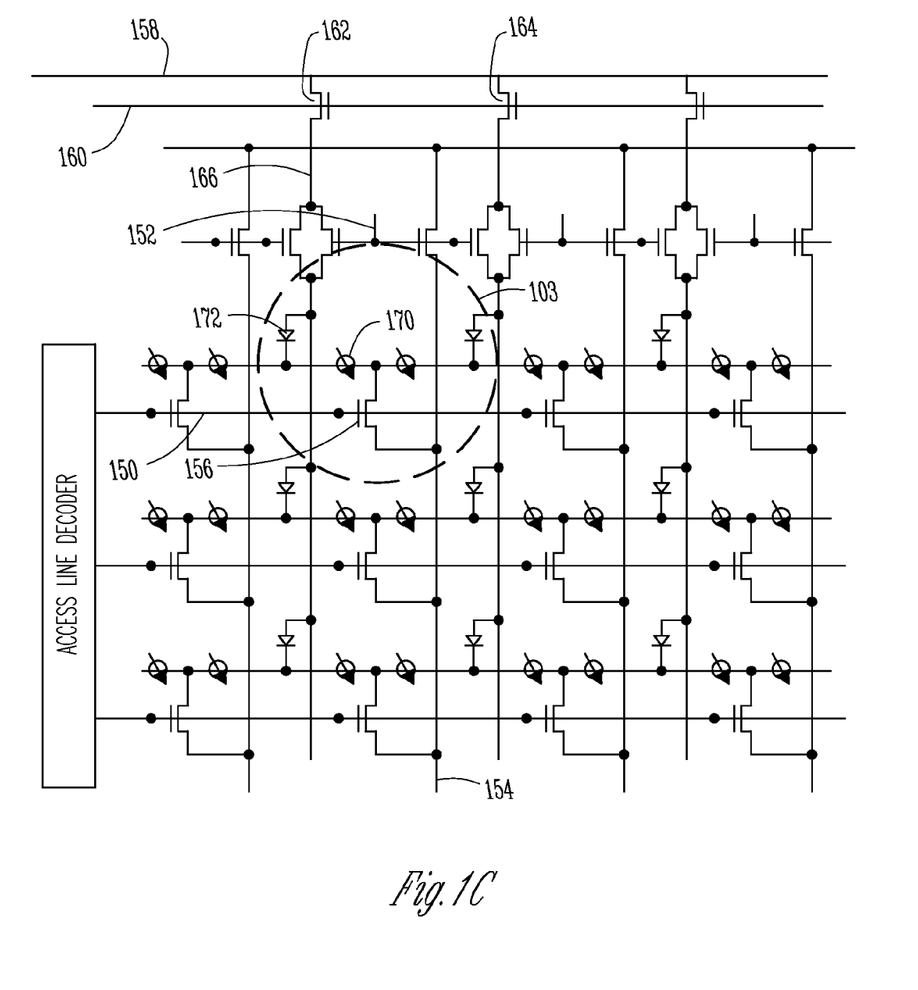
FIG. 1C shows a circuit diagram of a portion of a memory device similar to the memory device shown in FIG. 1A.

FIG. 1C illustrates a circuit diagram of a memory array similar to the array 100 illustrated in FIGS. 1A and 1B. A memory block 103 similar to the memory block 102 illustrated in FIGS. 1A and 1B is shown. A phase change cell 170 is illustrated.

In one method of operation, an access line 150 is activated to open gates of access transistors in the desired row, such as access transistor 156. In the embodiment illustrated in FIG. 1C, a block select line 152 is activated to select a transfer line 154. A first cell select signal is used on cell line 160 to select the first electrode select line 166. FIG. 1C illustrates a first transistor 162 and a second transistor 164 of opposite gate types. In one method of operation, the first electrode select line 166 is selected by driving cell select line 160 either high or low. By alternating gate types of transistors 162 and 164 in the array, half of the first electrode select lines 166 are enabled depending on whether cell select line 160 is driven high or low.

In the example shown in FIG. 1C, the phase change cell 170 is selected. A line 158, for example a constant voltage line, is coupled to the cell 170 and a signal travels through a rectifying device 172. The signal is further coupled to the phase change cell 170, and if the phase change cell is in a conductive state, the signal travels through the access transistor 156 and out to the transfer line 154.

In one embodiment, the rectifying device 172 as used with phase change cell 170 and the similar configuration throughout the array reduce or eliminate unwanted disturbances of other adjacent cells during operation of the array. The rectifying devices in the array stop signals, charges, etc. from traveling through other paths in the circuit and causing unwanted cell programming, noise, etc.

Figure 2A:
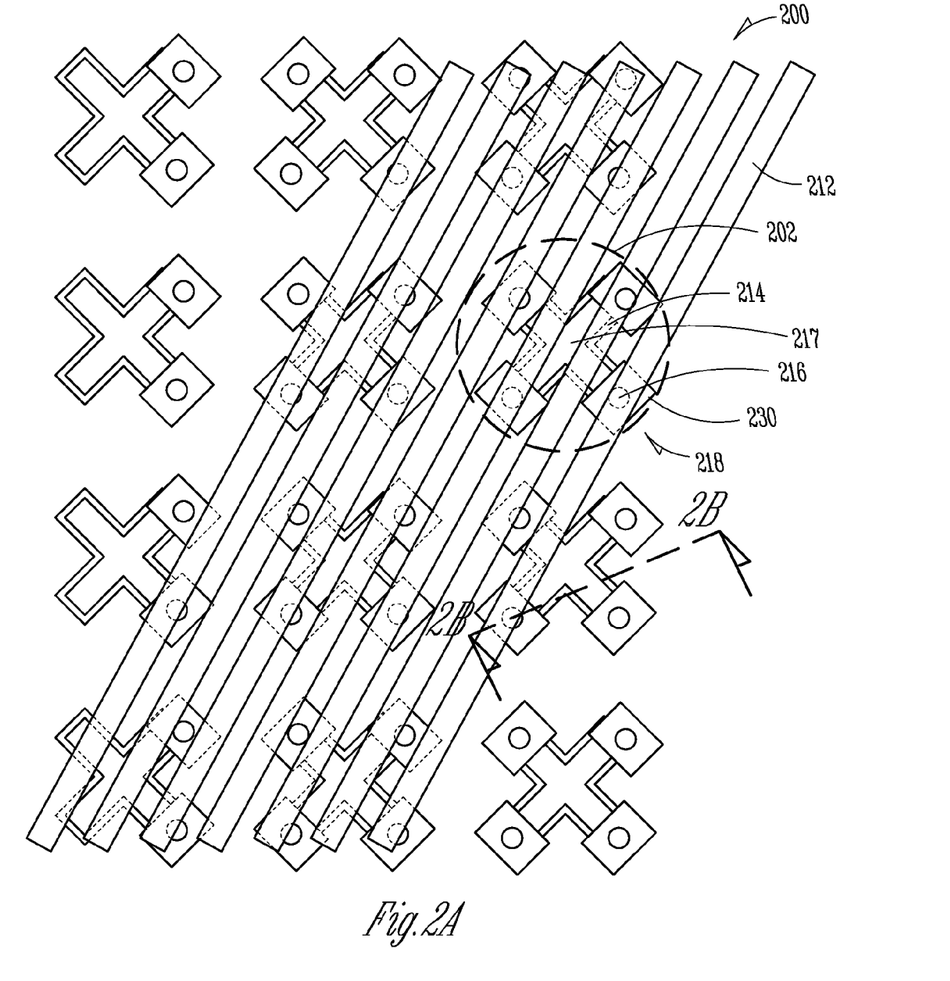
FIG. 2A shows a top view of another memory device according to an embodiment of the invention.

FIG. 2A illustrates another embodiment of a memory array 200. A block 202 is shown in the array 200. The block 202 is a multi-cell block that includes four cells associated with a single access transistor as will be shown in more detail in subsequent figures. Cell 218 is illustrated as one of the four cells in the block 202.

In one embodiment, the block 202 includes a phase change memory block. A phase change structure 214 is shown comprising the four cells. As stated in previous examples, an example of a phase change material includes a chalcogenide glass, although the invention is not so limited. A number of electrode select lines 212 are shown coupled to the cells in the array 200.

Figure 2B:
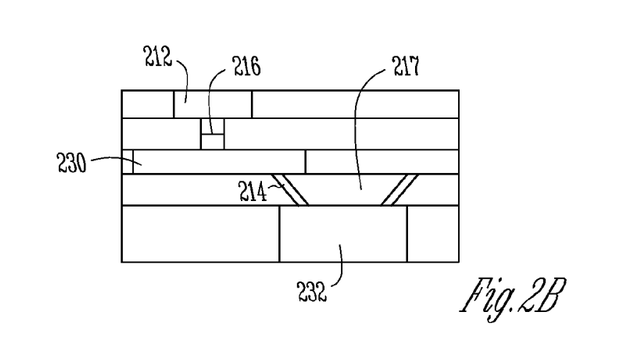
FIG. 2B shows a cross section of the memory device from FIG. 2A sectioned along line 2B-2B.

FIG. 2B illustrates the connection between the electrode select lines 212 and the phase change structure. An example cell similar to cell 218 is shown in FIG. 2B. A first electrode 230 is shown coupled to the phase change structure 214, which is in turn coupled to a second electrode 232. The second electrode 232 is in turn connected to an access transistor (not shown) in selected embodiments.

A dielectric 217 is shown adjacent to the phase change structure 214 to provide electrical isolation. In the example shown, the phase change structure 214 includes a cross like structure. Although a cross like structure is shown, the invention is not so limited.

A rectifying device 216 is also shown in FIGS. 2A and 2B. As discussed above, examples of rectifying devices include, but are not limited to, diodes, gate coupled field effect transistors, etc. One of ordinary skill in the art, having the benefit of the present disclosure, will recognize that any of a number of rectifying devices are possible. The rectifying device 216 is located between the electrode select line 212 and the first electrode 230. As discussed above, this configuration helps to isolate phase change cells during operation of the array, providing better reading and writing characteristics with fewer errors.

The configuration shown in FIGS. 2A and 2B illustrates a separate structure as a rectifying device 216 for each cell such as cell 218. A rectifying device for each cell provides increased isolation from adjacent cells and improved array performance.

Figure 2C:
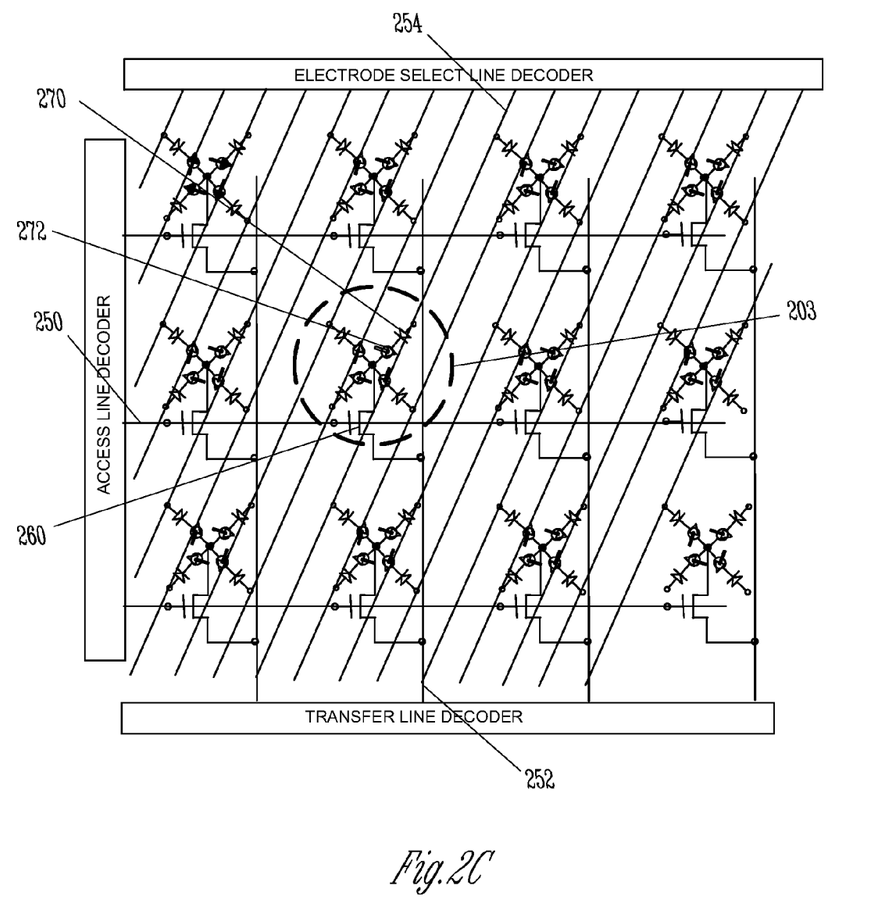
FIG. 2C shows a circuit diagram of a portion of a memory device similar to the memory device shown in FIG. 2A.

FIG. 2C illustrates a circuit diagram of a memory array similar to the array 200 illustrated in FIGS. 2A and 2B. A memory block 203 similar to the memory block 202 illustrated in FIGS. 2A and 2B is shown. As discussed above, the memory block 203 is a four cell phase change memory block.

In one method of operation, an access line 250 is activated to open gates of access transistors in the desired row, such as access transistor 260. In the embodiment illustrated in FIG. 2C, transfer line 252 is provided to transmit a signal to the transfer line sense circuitry such as a decoder and determine a state of the selected cell. In the embodiment shown, there are four cells associated with each access transistor. The memory block 203, for example, includes four phase change cells 272 each with an individual associated rectifying device 270.

Although a phase change memory device is described as an example, the invention is not so limited. Other embodiments of the present invention include multiple cell memory devices in general where more than one cell is associated with a single access transistor. Other multiple cell technologies may include examples such as magnetic storage cells, flash memory cells, etc.

In one embodiment, an electrode select line 254 is selected to select an individual cell within the block 203. The further selection of the desired access line 250 and transfer line 252 determine which block is written to or read.

In one embodiment, an electrode select line is selected according to a decode rule. In the example shown in FIGS. 2A-2C, a decode rule includes $L=2*m+4*n+k$. In this rule example, "m" is a row number in the memory array and "n" is a column number in the memory array. As described above, "m" and "n" determine a desired access transistor. In this rule example, "k" is an individual cell in the four cell memory block. Each cell "k" in this example is assigned a number from 1-4. In this rule example, "L" is an electrode select line number, with the first electrode select line on the left side of the circuit being labeled "1" and each following electrode select line to the right being incrementally numbered 2, 3, 4, etc.

Figure 3:
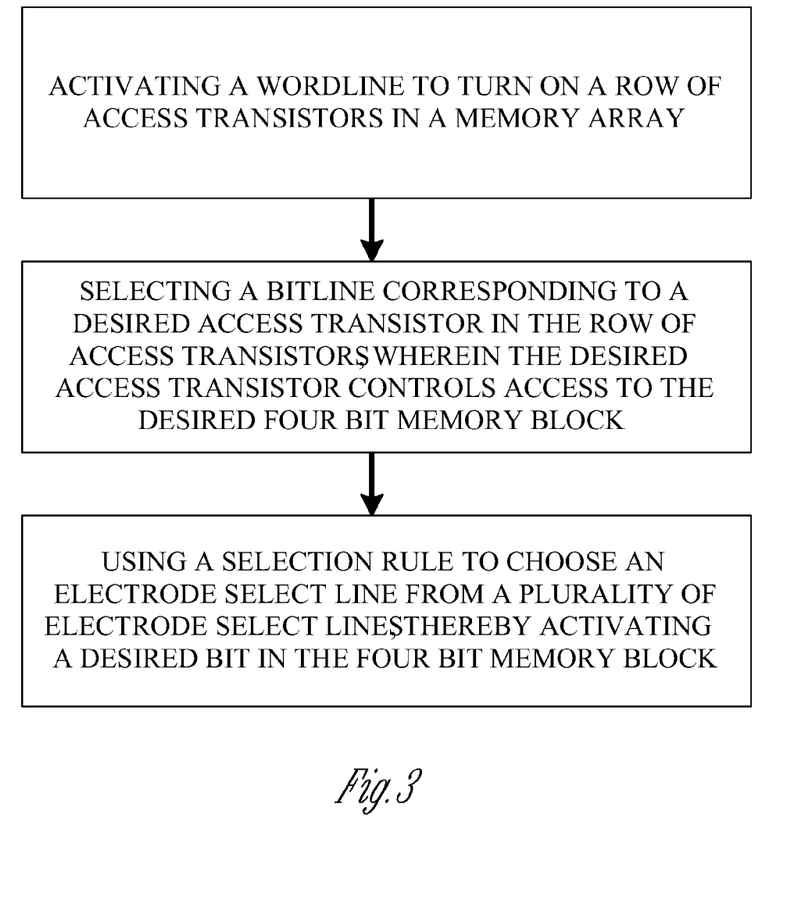
FIG. 3 shows a flow diagram of a method according to an embodiment of the invention.

FIG. 3 illustrates a method of operation of a memory array with four cells associated with each access transistor. One example of a memory array with four cells associated with each access transistor is illustrated in FIGS. 2A-2C as discussed above. Other examples are also illustrated in subsequent figures. As mentioned above, although a phase change memory is used as an example, selected embodiments are not limited to phase change memory configurations.

The operations in FIG. 3 are used to select a desired four cell memory block in an array of memory blocks. In the first operation, an access line is activated to turn on a row of access transistors in a memory array. In the second operation, a transfer line is selected that corresponds to a desired access transistor in the row of access transistors. In the third operation, an electrode select line is selected according to a decode rule such as the rule described above. Using the rule described above, only a single electrode select line is activated.

Figure 4A:
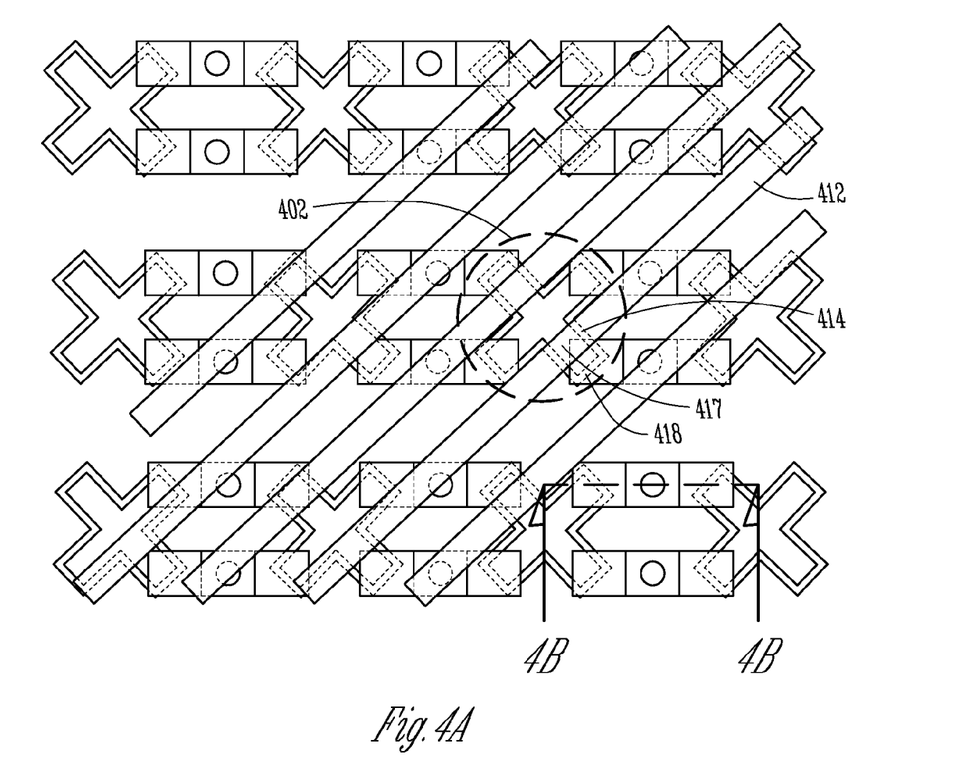
FIG. 4A shows a top view of another memory device according to an embodiment of the invention.

FIG. 4A illustrates another embodiment of a memory array. A block 402 is shown in the array. The block 402 is a multi-cell block that includes four cells associated with a single access transistor as will be shown in more detail in subsequent figures. Cell 418 is illustrated as one of the four cells in the block 402.

In one embodiment, the block 402 includes a phase change memory block. A phase change structure 414 is shown comprising the four cells. As stated in previous examples, an example of a phase change material includes a chalcogenide glass, although the invention is not so limited. A number of electrode select lines 412 are shown coupled to the cells in the array.

Figure 4B:
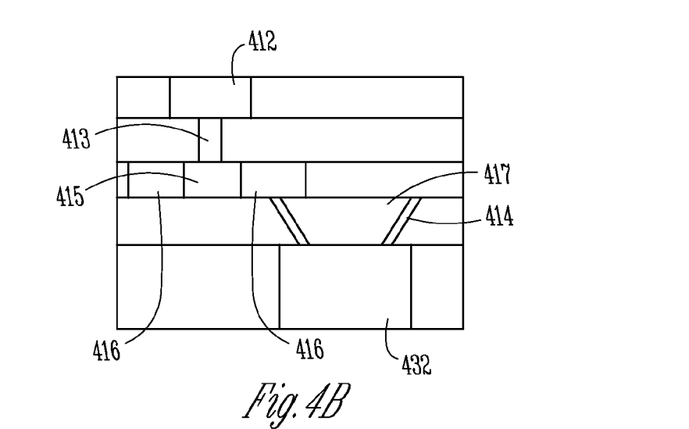
FIG. 4B shows a cross section of the memory device from FIG. 4A sectioned along line 4B-4B.

FIG. 4B illustrates the connection between the electrode select lines 412 and the components of the individual cells. An example cell similar to cell 418 is shown in FIG. 4B. A first type semiconductor portion 415 such as p-type material is shown coupled to a pair of second type semiconductor portions 416 such as n-type. In one example, the opposite type semiconductor materials form a rectifying device that provides increased cell isolation. The second type semiconductor portions 416 are shown coupled to the phase change structure 414, which is in turn coupled to a second electrode 432. The second electrode 432 is in turn connected to an access transistor (not shown) in selected embodiments. Alternatively, the second type semiconductor portions 416 are coupled to the phase change structure 414 through an additional conductive intermediate layer.

A dielectric 417 is shown adjacent to the phase change structure 414 to provide electrical isolation. In the example shown, the phase change structure 414 includes a cross like structure. Although a cross like structure is shown, the invention is not so limited.

As discussed above, the first type semiconductor portion 415 and the second type semiconductor portions 416 function as a rectifying device. The rectifying device is coupled to the electrode select line 412 using a contact 413. A contact, such as contact 413, is an embodiment of an electrode as recited in the following claims. The rectifying device is in turn coupled to the phase change structure 414. As discussed above, this configuration helps to isolate phase change cells during operation of the array, providing better reading and writing characteristics with fewer errors.

The configuration shown in FIGS. 4A and 4B illustrates one rectifying structure for every two cells such as cell 418. In the example shown in FIGS. 4A and 4B, there are two rectifying devices included in a single rectifying structure. A rectifying device for each cell provides increased isolation from adjacent cells and improved array performance.

Figure 4C:
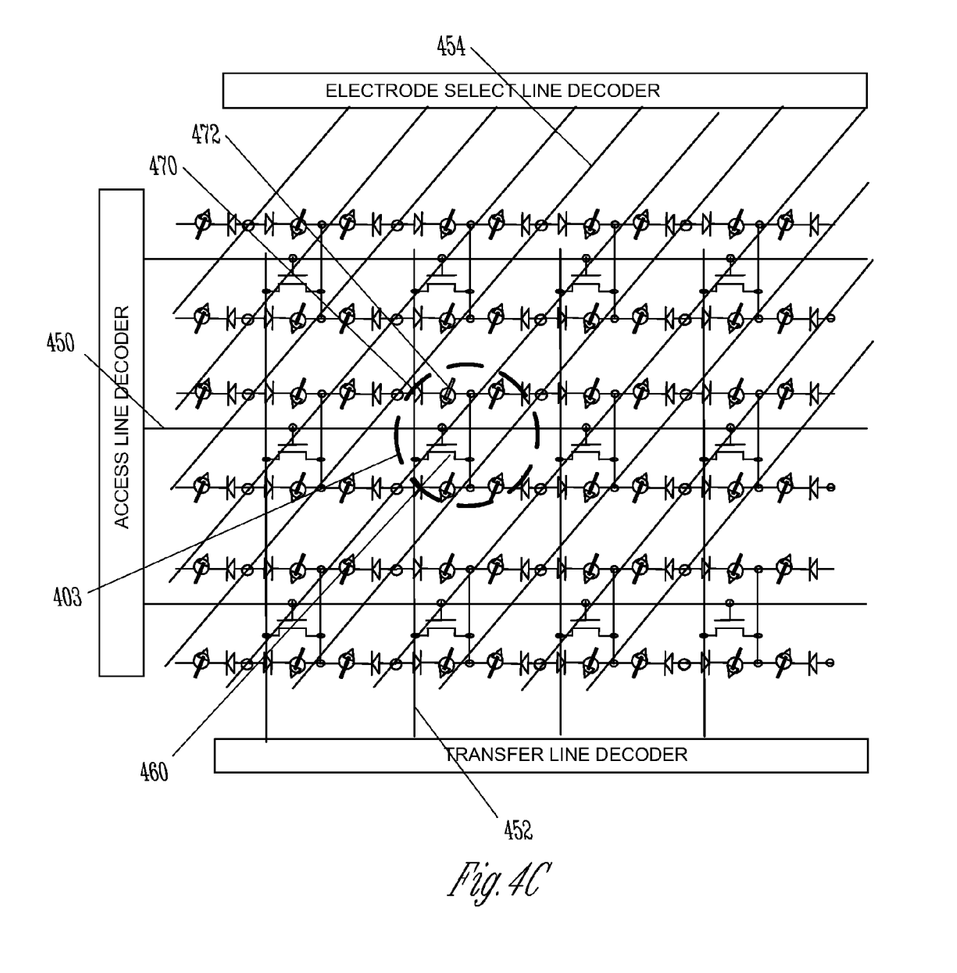
FIG. 4C shows a circuit diagram of a portion of a memory device similar to the memory device shown in FIG. 4A.

FIG. 4C illustrates a circuit diagram of a memory array similar to the array illustrated in FIGS. 4A and 4B. A memory block 403 similar to the memory block 402 illustrated in FIGS. 4A and 4B is shown. As discussed above, the memory block 403 is a four cell phase change memory block.

In one method of operation, an access line 450 is activated to open gates of access transistors in the desired row, such as access transistor 460. In the embodiment illustrated in FIG. 4C, transfer line 452 is provided to transmit a signal to the transfer line sense circuitry and determine a state of the selected cell. In the embodiment shown, there are four cells associated with each access transistor. The memory block 403, for example, includes four phase change cells 472 each with an individual associated rectifying device 470.

Although a phase change memory device is described as an example, the invention is not so limited. Other embodiments of the present invention include multiple cell memory devices in general where more than one cell is associated with a single access transistor. Other multiple cell technologies may include examples such as magnetic storage cells, flash memory cells, etc.

In one embodiment, an electrode select line 454 is selected to select an individual cell within the block 403. The further selection of the desired access line 450 and transfer line 452 determine which block is written to or read.

In one embodiment, electrode select lines are selected according to a selection rule. In the example shown in FIGS. 4A-4C, a decode rule includes $L=2*m+2*n+k$. In this rule example, "m" is a row number in the memory array and "n" is a column number in the memory array. As described above, "m" and "n" determine a desired access transistor. In this rule example, "k" is an individual cell in the four cell memory block. Each cell "k" in this example is assigned a number from 1-4. In this rule example, "L" is an electrode select line number, with the first electrode select line on the left side of the circuit being labeled "1" and each following electrode select line to the right being incrementally numbered 2, 3, 4, etc.

Figure 5A:
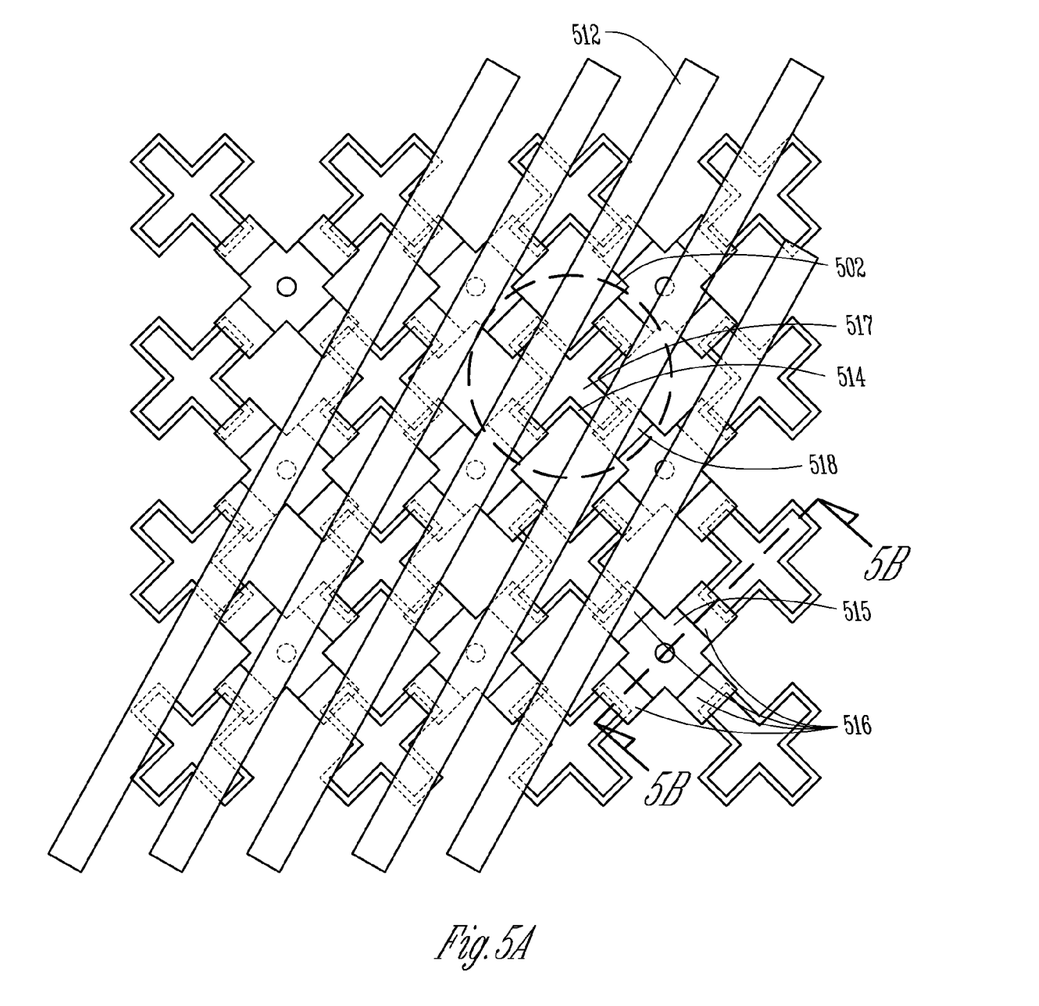
FIG. 5A shows a top view of another memory device according to an embodiment of the invention.

FIG. 5A illustrates another embodiment of a memory array. A block 502 is shown in the array. The block 502 is a multi-cell block that includes four cells associated with a single access transistor as will be shown in more detail in subsequent figures. Cell 518 is illustrated as one of the four cells in the block 502.

In one embodiment, the block 502 includes a phase change memory block. A phase change structure 514 is shown comprising the four cells. As stated in previous examples, an example of a phase change material includes a chalcogenide glass, although the invention is not so limited. A number of electrode select lines 512 are shown coupled to the cells in the array.

Figure 5B:
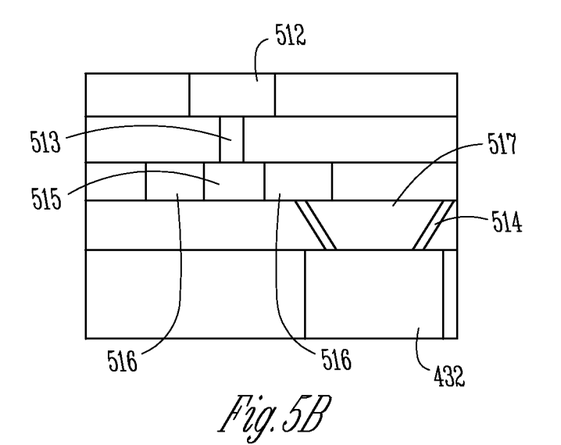
FIG. 5B shows a cross section of the memory device from FIG. 5A sectioned along line 5B-5B.

FIG. 5B illustrates the connection between the electrode select lines 512 and the components of the individual cells. An example cell similar to cell 518 is shown in FIG. 5B. A first type semiconductor portion 515 such as p-type material is shown coupled to a four second type semiconductor portions 516 such as n-type. In one example, the opposite type semiconductor materials form a rectifying device that provides increased cell isolation. The second type semiconductor portions 516 are shown coupled to the phase change structure 514, which is in turn coupled to a second electrode 532. The second electrode 532 is in turn connected to an access transistor (not shown) in selected embodiments. As described above, alternatively, the second type semiconductor portions 516 are coupled to the phase change structure 514 through an additional conductive intermediate layer.

A dielectric 517 is shown adjacent to the phase change structure 514 to provide electrical isolation. In the example shown, the phase change structure 514 includes a cross like structure. Although a cross like structure is shown, the invention is not so limited.

As discussed above, the first type semiconductor portion 515 and the second type semiconductor portions 516 function as a rectifying device. The rectifying device is coupled to the electrode select line 512 using a contact 513. The rectifying device is in turn coupled to the phase change structure 514. As discussed above, this configuration helps to isolate phase change cells during operation of the array, providing better reading and writing characteristics with fewer errors.

The configuration shown in FIGS. 5A and 5B illustrates one rectifying structure for every four cells such as cell 518. In the example shown in FIGS. 5A and 5B, there are four rectifying devices included in a single rectifying structure. A rectifying device for each cell provides increased isolation from adjacent cells and improved array performance.

Figure 5C:
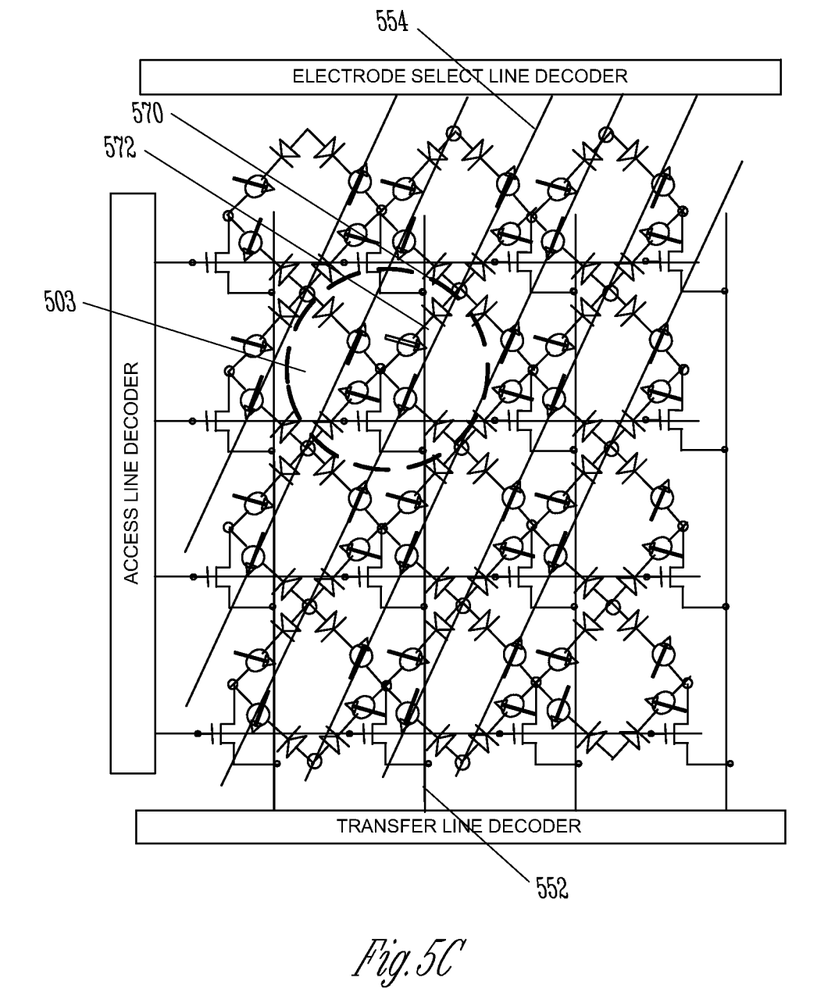
FIG. 5C shows a circuit diagram of a portion of a memory device similar to the memory device shown in FIG. 5A.

FIG. 5C illustrates a circuit diagram of a memory array similar to the array illustrated in FIGS. 5A and 5B. A memory block 503 similar to the memory block 502 illustrated in FIGS. 5A and 5B is shown. As discussed above, the memory block 503 is a four cell phase change memory block.

In one method of operation, an access line 550 is activated to open gates of access transistors in the desired row, such as access transistor 560. In the embodiment illustrated in FIG. 5C, transfer line 552 is provided to transmit a signal to the transfer line sense circuitry and determine a state of the selected cell. In the embodiment shown, there are four cells associated with each access transistor. The memory block 503, for example, includes four phase change cells 572 each with an individual associated rectifying device 570.

Although a phase change memory device is described as an example, the invention is not so limited. Other embodiments of the present invention include multiple cell memory devices in general where more than one cell is associated with a single access transistor. Other multiple cell technologies may include examples such as magnetic storage cells, flash memory cells, etc.

In one embodiment, an electrode select line 554 is selected to select an individual cell within the block 503. The further selection of the desired access line 550 and transfer line 552 determine which block is written to or read.

In one embodiment, an electrode select line is selected according to a decode rule. In the example shown in FIGS. 5A-5C, a decode rule includes $L=m+2*n+k-3$. In this rule example, "m" is a row number in the memory array and "n" is a column number in the memory array. As described above, "m" and "n" determine a desired access transistor. In this rule example, "k" is an individual cell in the four cell memory block. Each cell "k" in this example is assigned a number from 1-4. In this rule example, "L" is an electrode select line number, with the first electrode select line on the left side of the circuit being labeled "1" and each following electrode select line to the right being incrementally numbered 2, 3, 4, etc.

Although a number of examples are shown with various rectifying device architecture and associated electrode select line rules, the invention is not so limited. Additionally, although four cell per access transistor and two cell per access transistor embodiments are shown, the invention can be used with other multiple cell configurations. Using memory device configurations shown, and methods described herein, multiple cell memory devices are provided with improvements, including improved cell isolation for operations such as read and write. Further, methods and devices for addressing and accessing cells are shown that provide a simple and efficient way to manage devices with multiple cells associated with each access transistor. Using such configurations with a phase change memory provides high read and write speeds compared to other memories such as flash. Configurations as described herein further provide efficient device construction and selection of each phase change cell.

Figure 6:
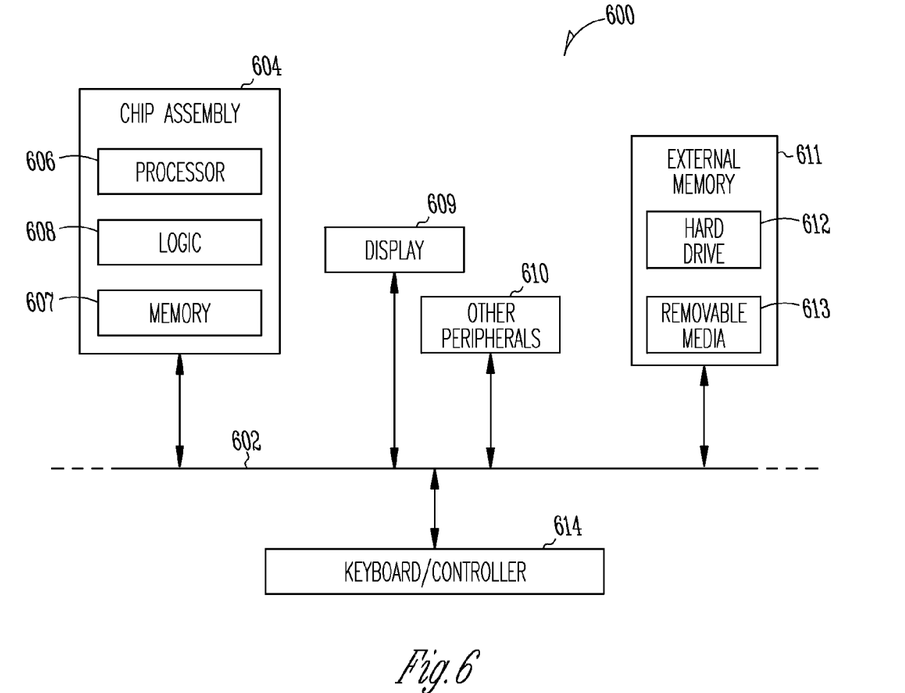
FIG. 6 shows an information handling system including a memory device according to an embodiment of the invention.

An embodiment of an information handling system such as a computer is included in subsequent figures to show an embodiment of a high-level device application for the present invention. FIG. 6 is a block diagram of an information handling system 600 incorporating at least one chip or chip assembly 604 that includes a memory device according to an embodiment of the invention. Information handling system 600 is merely one embodiment of an electronic system in which the present invention can be used. Other examples include, but are not limited to, personal data assistants (PDAs), cellular telephones, MP3 players, aircraft, satellites, military vehicles, etc.

In this example, information handling system 600 comprises a data processing system that includes a system bus 602 to couple the various components of the system. System bus 602 provides communications links among the various components of the information handling system 600 and may be implemented as a single bus, as a combination of busses, or in any other suitable manner.

Chip assembly 604 is coupled to the system bus 602. Chip assembly 604 may include any circuit or operably compatible combination of circuits. In one embodiment, chip assembly 604 includes a processor 606 that can be of any type. As used herein, "processor" means any type of computational circuit such as, but not limited to, a microprocessor, a microcontroller, a graphics processor, a digital signal processor (DSP), or any other type of processor or processing circuit.

In one embodiment, a memory chip 607 is included in the chip assembly 604. Those skilled in the art will recognize that a wide variety of memory device configurations may be used in the chip assembly 604. Acceptable types of memory chips include, but are not limited to, Dynamic Random Access Memory (DRAMs) such as SDRAMs, SLDRAMs, RDRAMs and other DRAMs. Memory chip 607 can also include non-volatile memory such as flash memory. In one embodiment, the memory chip 607 includes a phase change random access memory (PCRAM).

In one embodiment, additional logic chips 608 other than processor chips are included in the chip assembly 604. An example of a logic chip 608 other than a processor includes an analog to digital converter. Other circuits on logic chips 608 such as custom circuits, an application-specific integrated circuit (ASIC), etc. are also included in one embodiment of the invention.

Information handling system 600 may also include an external memory 611, which in turn can include one or more memory elements suitable to the particular application, such as one or more hard drives 612, and/or one or more drives that handle removable media 613 such as floppy diskettes, compact disks (CDs), digital video disks (DVDs), and the like. A memory constructed as described in examples above is included in the information handling system 600.

Information handling system 600 may also include a display device 609 such as a monitor, additional peripheral components 610, such as speakers, etc. and a keyboard and/or controller 614, which can include a mouse, trackball, game controller, voice-recognition device, or any other device that permits a system user to input information into and receive information from the information handling system 600.

While a number of embodiments of the invention are described, the above lists are not intended to be exhaustive. Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present invention. It is to be understood that the above description is intended to be illustrative and not restrictive. Combinations of the above embodiments, and other embodiments, will be apparent to those of skill in the art upon reviewing the above description. The scope of the invention includes any other applications in which the above structures and methods are used. The scope of the invention should be determined with reference to the appended claims, along with the full scope of equivalents to which such claims are entitled.

What is claimed is:

1. A memory device, comprising:
a first electrode;
a second electrode coupled to the first electrode through a resistance switching material, selectable between a first state, and a second state with higher resistance than the first state, wherein the resistance switching material forms a ring-like structure having a plurality of portions, and wherein each of the portions comprises a respective one of a plurality of cells of the memory device.

2. The memory device of claim 1, further comprising:
a rectifying device coupled to the first electrode.

3. The memory device of claim 2, further comprising:
an access transistor coupled to a side of the resistance switching material opposite from the rectifying device.

4. A memory device, comprising:
an electrode coupled to another electrode through a resistance switching material, selectable between a first state, and a second state with higher resistance than the first state, wherein the resistance switching material forms a ring-like structure having a plurality of portions, and wherein each of the portions comprises a respective one of a plurality of cells of the memory device; and
a rectifying device coupled to the other electrode.

5. The memory device of claim 4, wherein the plurality of cells comprises two cells.

6. The memory device of claim 4, wherein the plurality of cells comprises four cells.

7. The memory device of claim 4, wherein the rectifying device comprises a diode.

8. The memory device of claim 4, wherein the rectifying device comprises one of a plurality of rectifying devices.

9. The memory device of claim 4, wherein the rectifying device is located between an electrode select line and the other electrode.

10. The memory device of claim 4, wherein the rectifying device is located between the other electrode and the resistance switching material.

11. The memory device of claim 4, wherein the resistance switching material comprises a phase change material capable of changing between a first conductive phase and a second conductive phase that is less conductive than the first conductive phase.

12. The memory device of claim 11, wherein the phase change material comprises a chalcogenide glass.

13. A memory device, comprising:
a plurality of first electrodes; and
a plurality of multicell blocks, each including a plurality of second electrodes coupled to a respective one of the plurality of first electrodes by a resistance switching material capable of changing between a first conductive state and a second state that is less conductive than the first state, wherein the resistance switching material forms a ring-like structure having a plurality of portions, and wherein each of the portions comprises a respective one of a plurality of cells of the memory device.

14. The memory device of claim 13, further comprising:
a plurality of rectifying structures respectively coupled to the plurality of multicell blocks.

15. The memory device of claim 14, wherein the plurality of rectifying structures are located between a plurality of electrode select lines and the first electrodes.

16. The memory device of claim 14, wherein the plurality of rectifying structures are located between the plurality of first electrodes and a phase change material.

17. The memory device of claim 14, wherein the plurality of rectifying structures comprise a plurality of diodes.

18. The memory device of claim 14, wherein the plurality of rectifying structures comprise a plurality of rectifying devices for each multicell block.

* * * * *